United States Patent
Flükiger et al.

(10) Patent No.: US 7,766,549 B2
(45) Date of Patent: Aug. 3, 2010

(54) METHOD, SYSTEM AND DEVICE FOR AUTOMATED CONFIGURING OF AN X-RAY SOURCE APPARATUS

(75) Inventors: Charles Flükiger, Spiegel b. Bern (CH); Lothar Schultheis, Oftringen (CH)

(73) Assignee: Comet Holding AG, Flamatt (CH)

(*) Notice: Subject to any disclaimer, the term of this patent is extended or adjusted under 35 U.S.C. 154(b) by 179 days.

(21) Appl. No.: 11/992,059

(22) PCT Filed: Sep. 20, 2005

(86) PCT No.: PCT/EP2005/054713
§ 371 (c)(1),
(2), (4) Date: Mar. 14, 2008

(87) PCT Pub. No.: WO2007/038978
PCT Pub. Date: Apr. 12, 2007

(65) Prior Publication Data
US 2009/0080621 A1   Mar. 26, 2009

(51) Int. Cl.
*G01D 18/00* (2006.01)
(52) U.S. Cl. .................. 378/207; 378/117; 378/114; 378/101

(58) Field of Classification Search ............... 378/101, 378/109–112, 114, 115, 117, 207
See application file for complete search history.

(56) References Cited

U.S. PATENT DOCUMENTS

| 5,434,900 | A | 7/1995 | Tanaka et al. | |
| 6,325,540 | B1* | 12/2001 | Lounsberry et al. | 378/207 |
| 6,621,890 | B1 | 9/2003 | Rondeux | |
| 2003/0097229 | A1 | 5/2003 | Herrmann et al. | |

* cited by examiner

*Primary Examiner*—Courtney Thomas
(74) *Attorney, Agent, or Firm*—Reising Ethington P.C.

(57) ABSTRACT

A method, a system and a device for automated configuration of a high power X-ray source apparatus (10), which has multiple modules (20, 28, 30, 50, 53). A first module (20, 28, 30, 50, 53) of the high power X-ray source apparatus (10) has an identification unit (25, 27, 31, 52, 54) storing at least one parameter of the first module (20, 28, 30, 50, 53) and transmitting the parameters to a configuration control unit (60). At least one operating parameter of a second module (20, 28, 30, 50, 53) is determined by the configuration control unit (60) based on characteristics of the transmitted parameter of the first module (20, 28, 30, 50, 53). The high power X-ray source apparatus (10) is configured by setting the operating parameter of the second module (20, 28, 30, 50, 53) to the determined value.

28 Claims, 2 Drawing Sheets

METHOD, SYSTEM AND DEVICE FOR AUTOMATED CONFIGURING OF AN X-RAY SOURCE APPARATUS

FIELD OF THE INVENTION

The present invention relates generally to the field of X-ray source apparatus or X-ray source systems. More especially, the present invention relates to configuring of a high power X-ray source apparatus, which is set up having multiple modules. In particular, the present invention relates to a method, a system and a device for configuring a high power X-ray source apparatus, where operating parameters of a module are determined by a configuration control unit based on the parameters of at least one other module.

DESCRIPTION OF RELATED ART

X-ray source apparatus and X-ray source systems are nowadays widely used for various purposes. Most applications of these X-ray source apparatus and X-ray source systems are based on the ability of X-rays to penetrate and pass through non-transparent matter. The density and composition of the internal features of the exposed object alter the intensity of the transmitted X-rays. These alterations, in turn, can be detected by X-ray detectors, i.e. photographic films, known as radiographs.

One of the earliest and still very important applications of X-rays is in medicine, where radiography is used in both diagnosis and therapy. Diagnostic applications include the detection of bone fractures, foreign objects in the body, dental cavities, and tumours such as cancer, while, in therapeutic treatment, X-rays are often used to stop the spread of malignant tumours. In addition, X-rays are also valuable in industry as a means of non-destructive testing. X-ray images easily reveal the presence of flaws or cracks that could put human lives in danger. Thus, many industrial products are inspected routinely by means of X-rays, so that defective products may be eliminated at the point of production. Moreover, X-rays are widely used as a scientific research tool in physics, chemistry, mineralogy, metallurgy or biology. Security applications of X-rays include the scanning of luggage and passengers at airports, border crossings or similar places, where there is a need for increased security against hidden bombs or weapons, or, at customs points, a need for detection of fake or smuggled goods. Finally, X-rays are also used to determine the authenticity of works of art and for art restoration.

Conventional high power X-ray source apparatus can be operated in two different modes, according to their purpose and particular necessity. The first mode, called the radiographic mode, is used to produce a radiographic image, or a radiograph, as described above. In regular medical and industrial applications, the high power X-ray source apparatus are mostly operated in this mode. In the radiographic mode, the operating parameters of the X-ray tube (such as the operating current and/or operating voltage) are stored in the high power X-ray source apparatus, and cannot be modified or adjusted by the operator during exposure. However, the operator usually is allowed to adjust the time of exposure, i.e. the time during which the X-rays are applied to the scanned object. The second operating mode of a high power X-ray source apparatus is the so-called fluoroscopic mode. In the fluoroscopic mode, no operating parameters are preset, and the operator is allowed to change the parameters that matches his needs in an optimal manner during exposure.

Usually, high power X-ray source apparatus and high power X-ray source systems are not a single entity, but consist of multiple modules. These different modules usually comprise an X-ray tube, a high voltage (HV) generator, a high voltage cable for connecting the X-ray tube to the high voltage generator etc. Many high power X-ray source apparatus and high power X-ray source systems also contain a further module, a cooler, as the production of X-rays releases excessive heat within the X-ray tube which in turn has to be transported via a cooler to avoid damage. Furthermore, in most cases, these different modules of the high power X-ray source apparatus can be operated with different operational limits. Nevertheless, operational limits of different modules may not be identical. This fact can cause serious problems, and even lead to the destruction of one or all of the modules, if it is tried to operate a module beyond its operational limits. Therefore, a correct configuration of the high power X-ray source apparatus is of fundamental importance for their correct and safe use. This configuration has to be performed at least once prior to the first operation of the X-ray source apparatus. However, the configuration can be performed as many times as necessary, always in order to guarantee an optimal and safe functioning of the X-ray source apparatus.

In conventional X-ray source apparatus or X-ray source systems, this configuration is generally achieved using a conventional method. In this conventional method, a qualified practitioner is required for configuring the X-ray source apparatus before first start-up of said apparatus. This qualified practitioner checks and/or adjusts the range of operating parameters that can be modified by the operator in order to ensure that the high power X-ray source apparatus can never be used in an inappropriate manner. The disadvantage of this method, however, is that each new configuration of the high power X-ray source apparatus calls for help from a highly qualified practitioner. Understandably, this qualified person sometimes cannot be there right away, so the necessary reconfiguration and/or start-up of the high power X-ray source apparatus can be greatly delayed. Moreover, an incorrect configuration of the high power X-ray source apparatus can result in significant material damage, serious injuries or even loss of human lives.

The weakness of conventional configuration method for high power X-ray source apparatus or high power X-ray source systems can also be particularly well observed when it is necessary to replace one or more modules, i.e. owing to failure or for other reasons. High power X-ray source apparatus and high power X-ray source systems are often operated at remote locations, and it is often then difficult or impossible to get a qualified practitioner who can perform a proper configuration of the high power X-ray source apparatus. Moreover, important data documenting the actual functioning of the high power X-ray source apparatus leading up to the failure are usually available only for the X-ray source apparatus as a whole and/or only locally. A module returned to the producer usually does not contain these data. Nevertheless, failure data would be a very important tool for repairing the module and preventing future failures due to improper configuration or improper operating modus of the high power X-ray source apparatus.

A method for remotely configuring and servicing a field replaceable unit in a medical diagnostic system is disclosed in U.S. Pat. No. 6,325,540. This method comprises the steps of establishing a communication connection between the medical diagnostic system and a remote facility, communicating identification information from an electronic device coupled to the field replaceable unit to the remote facility, communicating configuration information from the remote facility to the medical diagnostic system and configuring the medical diagnostic system in accordance with the configuration information from the remote facility. However, this method does not provide a solution to the problem of finding an optimal operating parameters of a multiplicity of modules which can be employed to constitute a high power X-ray source apparatus. Moreover, this method does not provide for a verification of each module, prior to configuring the whole system.

SUMMARY OF THE INVENTION

It is thus a first and main object of the invention to provide a system, a method and a device for automated configuration of a high power X-ray source apparatus that are capable of fulfilling the above-discussed requirements and which do not have the mentioned drawbacks.

These and still other objects of this invention are attained by the method, the system and the device for automated configuring of a high power X-ray source apparatus as defined in the independent claims. Further special or preferred embodiments follow moreover from the dependent claims and from the specification.

The above-mentioned objects are achieved through the present invention in that, in a method for automated configuring of a high power X-ray source apparatus, the high power X-ray source apparatus being set up having multiple modules, in which a multiplicity of modules of the high power X-ray source apparatus comprises an identification unit, whereby identification and/or nominal parameters of the module are stored in the identification unit of the respective module, an acceptable set of parameters for each of the multiplicity of modules is stored in a database of a configuration control unit, at least one identification and/or nominal parameter of each of the multiplicity of modules is transmitted from the identification unit of the respective module to a configuration control unit, the transmitted parameters of the multiplicity of modules are compared with the acceptable parameter set from the database by means of the configuration control unit and each module is authenticated if the transmitted parameters of the module match the acceptable parameter set of the database, at least one operating parameter of at least one module is determined by means of the configuration control unit based on if the transmitted parameters of the multiplicity of modules, and the high power X-ray source apparatus is automatically configured by setting the determined operating parameter of the module. The identification and/or nominal parameters of the module can comprise not only identification parameters such as a unique registration number, serial number, type, model identification, producer identification etc., but also operating parameters which are necessary for an efficient and safe operation of each given module. A more detailed and precise characterization of the module is thereby possible.

Such a method has the advantage that the operating parameter of a module of the high power X-ray source apparatus is determined and set based on characteristics of parameters of at least one other module of the X-ray source apparatus. No inconsistent configuration is possible. Such a method results in much better performance and lower costs for users of high power X-ray source apparatus, since no qualified operator is needed for configuration of the high power X-ray source apparatus. Moreover, such a method has the advantage, among other things, that each module is authenticated before configuring the high power X-ray source apparatus. Only modules with parameters that match a pre-defined and pre-stored acceptable set of parameters can be successfully operated. Thus, only modules presenting no risk to the high power X-ray source apparatus or to the life of the operators or patients or other persons can be used. In addition, counterfeit equipment, so-called bogus parts, or otherwise faulty pieces can be automatically excluded.

In an embodiment variant, the at least one operating parameter of the at least one module is determined as the minimum of the transmitted parameters of a multiplicity of modules. This embodiment variant has the advantage, among other things, that the operating parameter of the module cannot be set to a value which is higher than the highest value permitted by each of the individual modules. The configuration of the high power X-ray source apparatus can thus be kept consistent for any given constellation of modules.

In another embodiment variant, the identification and/or nominal parameters of the module stored in the identification unit of the respective module comprise maximum operating voltage and/or maximum operating current and/or maximum operating power and/or maximum operating filament current and/or typical operating filament voltage. This embodiment variant has the advantage, among other things, that the most relevant parameters are stored in the identification unit of the module. These parameters can be used for determining the optimal operational mode of the module in the high power X-ray source apparatus.

In a further embodiment variant, after configuring the high power X-ray source apparatus, at least one actual operating parameter of the module is stored in a continuous way in the identification unit of the respective module. This embodiment variant has the advantage, among other things, that the identification unit of the module saves all pertinent parameters of the module, making it possible for them to be further used or evaluated. Furthermore, actual (i.e. measured) operating parameters are gathered during the operation of the high power X-ray source apparatus and stored locally in the identification unit of the given module. The history and the evolution of the operating parameters can be easily established and utilized. Thus, no data can get lost when removing or replacing the module in the high power X-ray source apparatus. The stored parameters can be further used, i.e. for evaluation of the function of the given module.

In another embodiment variant, the actual operating parameters of the module being stored in the identification unit of the respective module comprise the actual voltage and/or actual current and/or actual power and/or actual filament current. This embodiment variant has the advantage, among other things, that the most relevant operating parameters of a module are stored in the identification unit of the module. These parameters are the key values for a further evaluation of the operation of the high power X-ray source apparatus.

In still another embodiment variant, error log data are stored in the identification unit of the respective module. This embodiment variant has the advantage, among other things, that errors in functioning of each module can easily be tracked and evaluated. Necessary improvements and/or modifications can be carried out based on the stored data.

In a further embodiment variant, an acceptable parameters sets stored in a database of the configuration control unit comprise a value range. This embodiment variant has the advantage, among other things, that deviations in the parameter value (such as those due to natural aging processes, imperfect data gathering or measuring equipment, etc.) do not negatively influence the authentication of the modules. Moreover, some parameters may have admissible values comprising a whole range, which then can be managed properly.

In another embodiment variant, the transmitted parameter of the module are encrypted. This embodiment variant has the advantage, among other things, that no unauthorized person, company or society can get access to the transmitted parameters. The authenticity can be double-checked and the risk of counterfeit or bogus equipment is even further decreased.

In a further embodiment variant, the configuration control unit is external to the high power X-ray source apparatus. This embodiment variant has the advantage, among other things, that the operating of the configuration control unit can be observed and/or influenced directly by external operators. Different controlling programs can be used for different situations or constellations. Potential problems can easily be identified and solved.

In another embodiment variant, the configuration control unit is integrated in the module. This embodiment variant has the advantage, among other things, that no additional infrastructure is needed. Even existing high power X-ray source apparatus can be equipped to carry out the automated configuration of the X-ray source apparatus according to the present invention.

In yet another embodiment variant, the at least one parameter of the module is transmitted to the configuration control unit wirelessly. This embodiment variant has the advantage, among other things, that no wired connection is needed for transmitting the parameters from the respective modules to the configuration control unit. A potential failure of the transmission lines can be avoided. A much higher flexibility in the arrangement of the modules is possible. The configuration control unit can be placed in a remote position and still fulfill the required functionality.

In another embodiment variant, the module is an X-ray tube. This embodiment variant has the advantage, among other things, that optimal configuration of the X-ray source apparatus to match the X-ray tube characteristics can be achieved. Nominal operating parameters of the X-ray tube can be stored in the identification unit to help determine the correct and consistent configuration of the other modules of the high power X-ray source apparatus, while actual operating parameters can be stored in the identification unit during the operation of the high source X-ray source apparatus, providing for a way to evaluate and potentially improve the operating mode of the X-ray tube and the whole high power X-ray source apparatus.

At this point, it should be stated that, besides the method for configuring a high power X-ray source apparatus according to the invention, the present invention also relates to a system and a device for carrying out the method.

BRIEF DESCRIPTION OF THE DRAWINGS

Other features and advantages of the invention will become apparent from the following description of an embodiment thereof, as a non-limiting example, when read in connection with the accompanying drawing in which.

DETAILED DESCRIPTION OF EMBODIMENTS OF THE INVENTION

Figure 1:
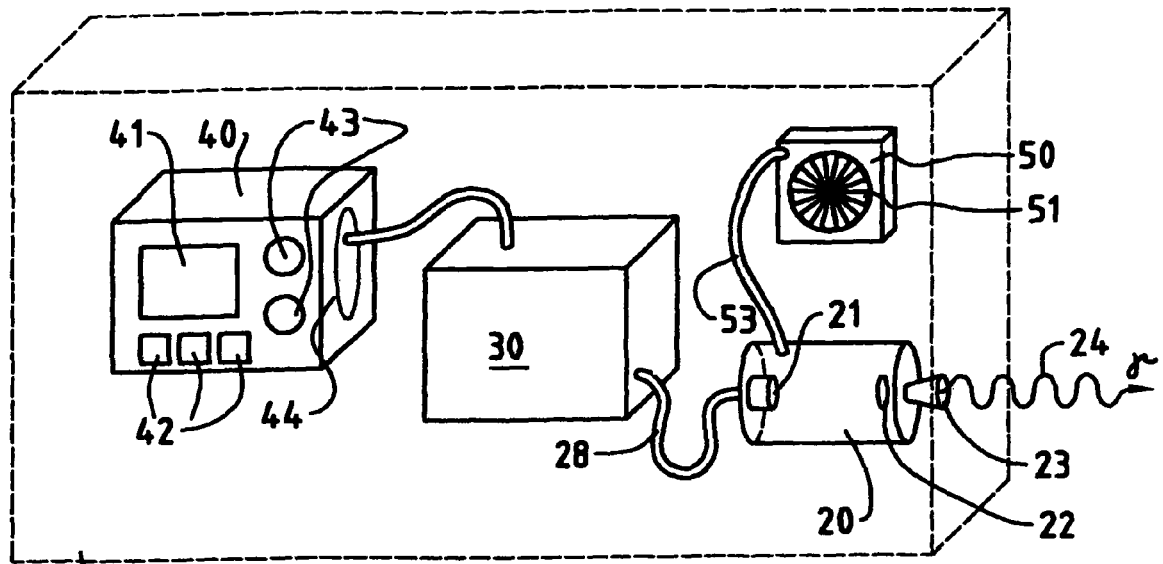
FIG. 1 shows a conventional high power X-ray source apparatus being set up having multiple modules.

FIG. 1 shows a conventional high power X-ray source apparatus 10 being set up having multiple modules 20, 28, 30, 50, 53. In FIG. 1, the reference numeral 20 represents an X-ray tube and the reference numeral 30 a high voltage (HV) generator. The X-ray tube is connected with the high voltage (HV) generator by means of the high voltage (HV) cable 28. This high voltage (HV) cable 28 feeds the X-ray tube 20 with the electrical power required for operation of the X-ray tube 20. The conventional high power X-ray source apparatus 10 further comprises a cooler which in FIG. 1 is represented by the reference numeral 50. The cooler 50 is an optional module in the conventional high power X-ray source apparatus 10. The cooler 50 is connected to the X-ray tube 20 by means of a cooler cable 53.

The X-ray tube 20 produces the radiation 24 used for exposing the object of interest placed properly in front of the X-ray source apparatus 10. The X-ray tube comprises a cathode 21 and an anode or target 22, arranged opposite each other in a vacuum tube. Heating the filament within an X-ray tube and applying a high voltage between the cathode connected with the filament and the anode 22 of the X-ray tube 20 gives rise to an electric current flowing from the cathode 21 to the target part of the anode 22. This current consists of free electrons accelerated freely in space and having an energy given by the voltage between the cathode and anode. Electrons impinging on the surface of the anode (i.e. target part) are strongly decelerated in inner electric fields of the target atoms thus giving rise to x-rays the so-called 'Bremsstrahlung'. In addition, characteristic X-ray photons are generated via impact-excitation of the inner electrons of the target atoms and subsequent radiative transition back to the ground state. The thus generated X-rays 24 leave finally the X-ray tube 20 through the window 23.

The penetrating power of X-rays depends essentially on their energy, and this is why conventional high power X-ray source apparatus 10 also comprise a unit 40 for controlling the operating mode of the high power X-ray source apparatus 10. The controlling unit 40 comprises, on the one hand, display means 41 for displaying and representing nominal and/or actual operating parameters of the high power X-ray source apparatus 10. The operational information about the high power X-ray source apparatus 10 can in particular comprise the nominal current and/or nominal voltage and/or nominal power and/or nominal filament current of the X-ray tube 20, but also any other nominal operating parameter of the X-ray tube 20 or of any other module 20, 28, 30, 50, 53 of the high power X-ray source apparatus 10. Actual operating parameters of the X-ray tube 20 can comprise in particular the actual current and/or actual voltage and/or actual power and/or actual filament current of the X-ray tube 20, but also, as described above, any other actual operating parameter of the X-ray tube 20 or of any other module 20, 28, 30, 50, 53 of the high power X-ray source apparatus 10. The controlling unit 40 further comprises controlling means 42/43 for putting the X-ray source apparatus 10 into service and setting the required operational values of the X-ray source apparatus 10, such as required operating power, required operating voltage, required operating current and/or required operating filament current. The operator of the X-ray source apparatus 10 is thus enabled to carry out different commands manipulating the controlling unit 40. Especially, in the fluoroscopic operating mode of the high power X-ray source apparatus 10, the controlling unit 40 is used for setting the above-mentioned and/or other operating parameters of the high power X-ray source apparatus 10. The controlling unit 40 is connected to the high voltage (HV) generator 30, whereby the commands set by the operator of the high power X-ray source apparatus 10 by means of the controlling unit 40 are transmitted to, and executed by, the high voltage (HV) generator 30.

Figure 2:
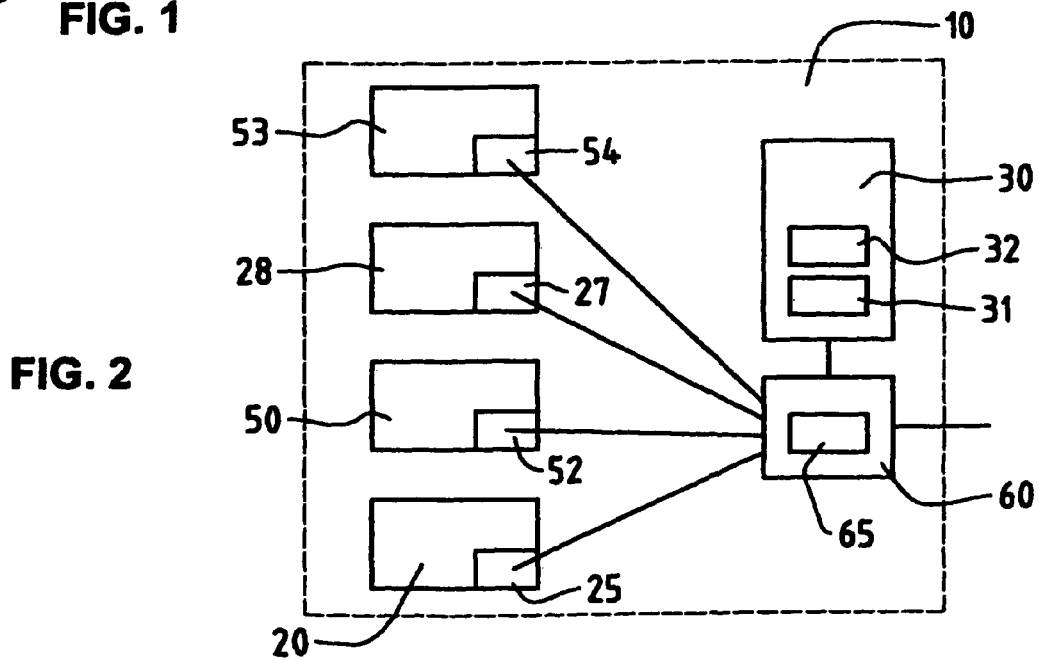
FIG. 2 shows a block diagram representing schematically a particular embodiment of a high power X-ray source apparatus according to the invention.

FIG. 2 shows schematically a particular embodiment of the high power X-ray source apparatus 10 being set up having multiple modules 20, 28, 30, 50, 53 according to the present invention. Each of the modules 20, 28, 30, 50, 53 of the high power X-ray source apparatus 10 comprises an identification unit 25, 27, 31, 52, 54. This identification unit 25, 27, 31, 52, 54 stores one or more parameters of the respective module 20, 28, 30, 50, 53. These stored parameters can comprise both identification parameters such as serial number, identification number, type or model number, producer identification and/or operating parameters, in particular maximal operating current, maximal operating voltage, maximal operating power and/or maximal operating filament current. The identification unit 25, 27, 31, 52, 54 can be either a hardware unit connected to, or integrated in, the module 20, 28, 30, 50, 53 or a software unit integrated into the operating software of the module 20, 28, 30, 50, 53. In particular, used as the identification unit 25, 27, 31, 52, 54 can be a computer chip known under the name iButton®, produced by Maxim Integrated Products (www.maxim-ic.com).

Figure 3:
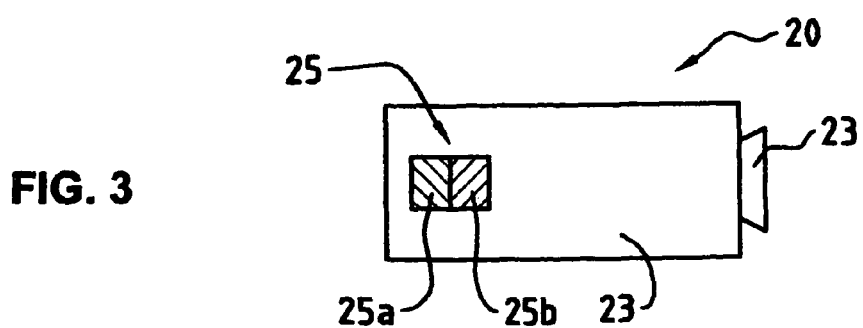
FIG. 3 shows a block diagram representing schematically the X-ray tube of a particular embodiment of the high power X-ray source apparatus according to the invention.

FIG. 3 shows schematically the X-ray tube of a particular embodiment of the high power X-ray source apparatus 10 being set up having multiple modules 20, 28, 30, 50, 53 according to the present invention. Similar or equivalent structure apply also for other modules 28, 30, 50, 53 of the high power X-ray source apparatus 10 according to the present invention. The X-ray tube 20 according to a particular embodiment of the present invention comprises an identification unit 25. The identification unit 25 of the X-ray tube 20 comprises two different segments 25a and 25b, whereby the division into these two segments 25a and 25b can be either physical (e.g. two segments supported by two different chips) or logical (e.g. one single chip with two logical segments). The identification unit 25 of the X-ray tube 20 stores different parameters of the X-ray tube 20. In a preferred embodiment, the identification unit 25 of the X-ray tube 20 stores identification parameters and/or operating parameters of the X-ray tube 20. On one side, each identification unit 25 of the X-ray tube 20 stores the hard-coded and unalterable unique registration code required for the correct addressing of the identification unit 25 of the X-ray tube 20. Other identification parameters and/or operating parameters of the X-ray tube 20 comprise parameters pre-defined by the producer of the X-ray tube 20 at the production and/or distribution time. These identification parameters and/or operation parameters of the X-ray tube 20 are stored in the read-only segment 25a of the identification unit 25. Modification of the stored identification and/or operating parameters of the X-ray tube 20 are nevertheless still possible, but can be performed only by authorised and qualified persons. The authorisation for access to the parameters stored in this read-only segment 25a of the identification unit 25 can be controlled by means of known authorisation methods, such as passwords, access codes, bar codes, authorisation cards or virtual authorisation certificates. This authorisation requirement guarantees that no important parameters can be modified or even deleted by accident or by unprofessional handling of the X-ray tube 20. On the other hand, the read-write segment 25b of the identification unit 25 can store actual operating parameters of the X-ray tube 20. These actual operating parameters can be continuously stored in the read-write segment 25b of the identification unit 25 during operation of the X-ray tube 20, and in particular can comprise, among other things, the actual operational voltage, the actual operational current, the actual operational power and/or the actual operational filament current.

Figure 4:
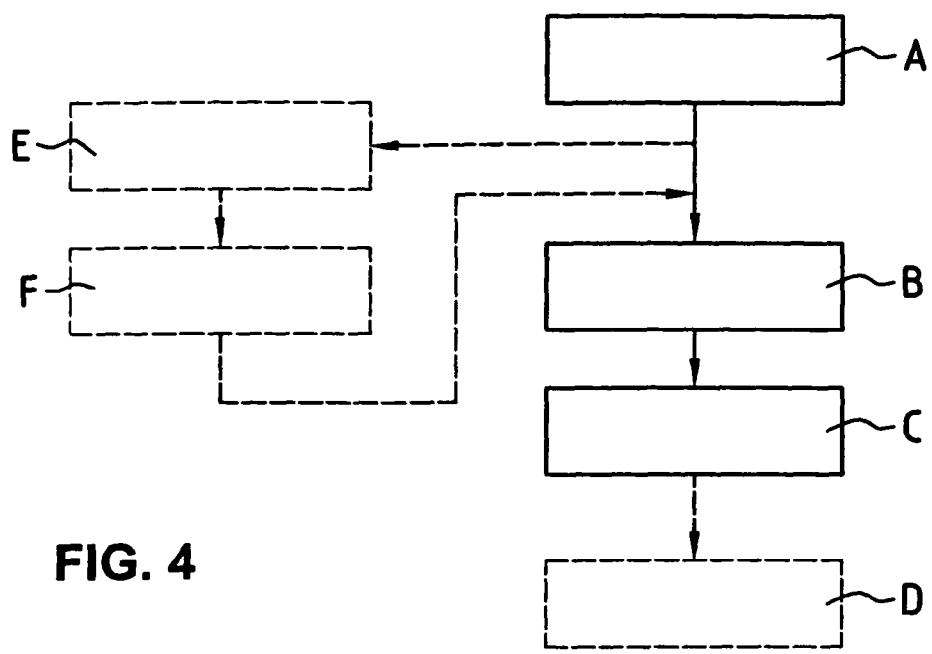
FIG. 4 shows a block diagram illustrating schematically a possible sequence of steps for configuration of a high power X-ray source apparatus according to a particular embodiment of the invention.

FIG. 4 illustrates the steps of the automated configuration method according to a particular embodiment of the present invention. According to this automated method, the high power X-ray source apparatus 10 is configured before putting it into service. In the automated method according to a particular embodiment of the present invention, at least one first module 20, 28, 30, 50, 53 of the high power X-ray source apparatus 10 comprises an identification unit 25, 27, 31, 52, 54, whereby this identification unit 25, 27, 31, 52, 54 comprises at least one parameter of the respective module 20, 28, 30, 50, 53. In a particular embodiment of the present invention, the X-ray tube 20 comprises an identification unit 25 with the identification parameters and nominal operating parameters of the X-ray tube 20. In particular these parameters comprise, among other things, the maximum operating voltage, the maximum operating current, the maximum operating power and the maximum filament current of the particular X-ray tube 20. At step A of the automated method, at least one of the parameters of the X-ray tube 20 is transmitted from the identification unit 25 of the X-ray tube to the configuration control unit 60. The configuration control unit 60 can preferably be integrated in the controlling unit 40 of the high power X-ray source apparatus 10. Nonetheless, the configuration control unit 60 can likewise be built as a separate entity or even integrated in any one of the modules 20, 28, 30, 50, 53 of the high power X-ray source apparatus 10.

At step B of the automated method according to a particular embodiment of the present invention, at least one operating parameter of the high voltage (HV) generator 30 is determined by means of the configuration control unit 60 based on the characteristics of the transmitted parameter of the X-ray tube 20. As an example, the maximum operating voltage of the high voltage (HV) generator 30 can be determined by the configuration control unit 60 based on the maximum operating voltage of the X-ray tube 20. As a matter of fact, the high voltage (HV) generator 30 is usually capable of providing a large range of different voltage values such that the nominal maximum operating voltage of the high voltage (HV) generator 30 is higher than the maximum operating voltage of the X-ray tube 20. Thus, at this step B, the maximum allowed operating voltage of the high voltage (HV) generator 30 is determined to be equal to the maximum operating voltage of the X-ray tube 20. Otherwise, the high voltage (HV) generator 30 could supply to the X-ray tube 20 a voltage higher than the maximal operating voltage of the X-ray tube 20 which would result in material damage or even a complete breakdown of the X-ray tube 20. The same reasoning applies to other operating parameters of the high voltage (HV) generator 30, in particular to the maximum operating current and/or maximum operating power. In the same manner, any other module 20, 28, 30, 50, 53 of the high power X-ray source apparatus 10 can be configured based on the identification parameters and/or operating parameters of any other module 20, 28, 30, 50, 53 of the high power X-ray source apparatus 10. At this same step B of the automated method according to a particular embodiment of the present invention, the at least one operating parameter of the high voltage (HV) generator 30 can be determined by means of the configuration control unit 60 based on the characteristics of the transmitted parameter of a plurality of modules 20, 28, 30, 50, 53 of the high power X-ray source apparatus 10. In particular, as an example, the maximum operating voltage of the high voltage (HV) generator 30 can be determined by the configuration control unit 60 based on the maximum operating voltage of the X-ray tube 20 and the high voltage (HV) cable 28. In any case, the maximum operating voltage of the high voltage (HV) generator 30 must be set to the lowest value of the maximum operating voltage of the multiplicity of modules 20, 28, 30, 50, 53. Nevertheless, this maximum operating voltage cannot be higher than the maximum nominal operating voltage of the high voltage (HV) generator itself. In the same manner, other operating parameters of the high voltage (HV) generator 30 can be determined by the configuration control unit 60 based on the transmitted corresponding operating parameters of the multiplicity of the modules 20, 28, 30, 50, 53 of the high power X-ray source apparatus 10.

Figure 5:
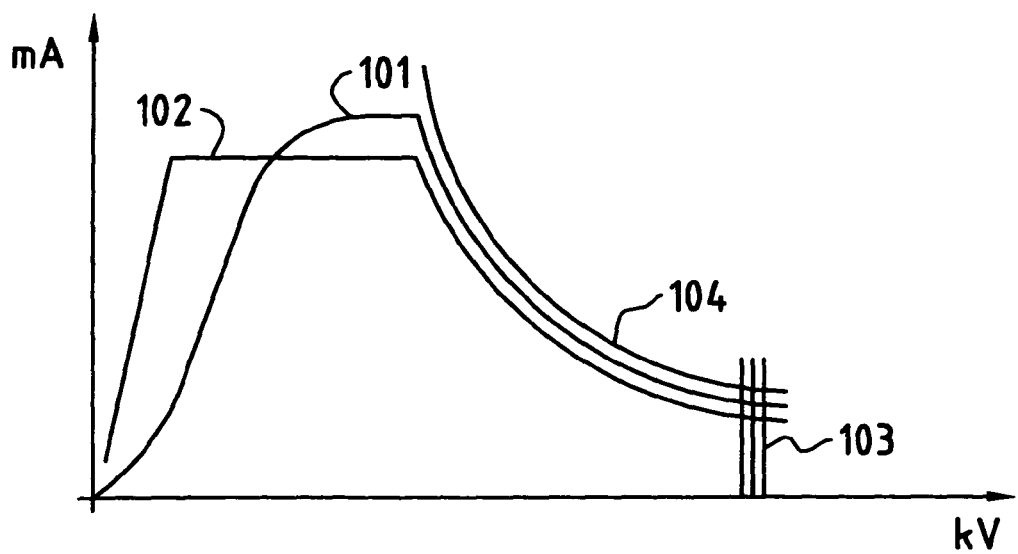
FIG. 5 illustrates one particular example of the configuration principles for the high power X-ray source apparatus using a graph representing the evolution of the current in various modules of the high power X-ray source apparatus as a function of the applied voltage.

FIG. 5 illustrates one particular example of the configuration principles for the high power X-ray source apparatus 10 on the basis of a graph representing the evolution of the current in various modules of the high power X-ray source apparatus 10 as a function of the applied voltage. In FIG. 5, the reference numeral 101 represents a typical current-voltage limit of the X-ray tube 20, the reference numeral 102 a current-voltage limit of the high voltage (HV) generator 30, the reference numeral 103 the voltage limit of the high voltage (HV) cable 28 and the reference numeral 104 a typical current-voltage limit (given by the maximal cooling power) for the cooler 50. In this particular example, the maximum operating voltage of the high power X-ray source apparatus 10 has to be set to the smallest value among the maximum nominal operating voltage values of the X-ray tube 20, the high voltage (HV) cable 28 and the high voltage (HV) generator 30. In the same manner, the maximum operating power of the high voltage X-ray source apparatus 10 has to be set to the smallest value among the maximum nominal operating power values of the X-ray tube 20, the high voltage (HV) generator 30 and the cooler 50. Finally, the maximum operating current of the high power X-ray source apparatus 10 has to be set to the smallest value among the maximum nominal operating current values of the X-ray tube 20 and the high voltage (HV) generator 30.

Back to FIG. 4, at step C of the automated method according to a particular embodiment of the present invention, the high power X-ray source apparatus 10 is configured by the configuration control unit 60 whereby the one or more operating parameters of the one or more modules 20, 28, 30, 50, 53 determined at the previous step is set to the determined value. A consistent configuration is thus ensured, and a safe putting into service and use of the high power X-ray source apparatus 10 is guaranteed.

According to another embodiment of the present invention, after the high power X-ray source apparatus 10 has been configured as described above and put into service, the actual operating parameters of one or various modules 20, 28, 30, 50, 53 are stored in the read-write segment of the respective identification unit 25, 27, 31, 52, 54 at step D. As an example, the actual operating current and/or actual operating voltage and/or actual operating power and/or actual operating filament current of the X-ray tube 20 are stored in the identification unit 25 of the X-ray tube 20. In the same manner, other actual operating parameters of the X-ray tube 20 can be stored in the identification unit 25 of the X-ray tube 20 during operation of the X-ray tube 20. Similarly, actual operating parameters of other modules 20, 28, 30, 50, 53 can be stored in the respective identification units 25, 27, 31, 52, 54. The identification units 25, 27, 31, 52, 54 can in the same way store error logs produced whenever operating errors occur during the operating of the high power X-ray source apparatus 10. These actual operating parameters and/or error logs can be analyzed afterwards by qualified persons, i.e. in order to discover possible reasons for a failure of the particular module 20, 28, 30, 50, 53.

According to a further embodiment of the present invention, an additional check can be performed in order to guarantee safe use of the high power X-ray source apparatus 10. According to this particular embodiment of the present invention, at step E in FIG. 4, before determining the operating parameters of a module 20, 28, 30, 50, 53 based on the transmitted operating parameters of another module 20, 28, 30, 50, 53, the one or more transmitted parameter of the first module 20, 28, 30, 50, 53 is compared with an acceptable parameter set from a database by means of the configuration control unit 60. The database can be implemented as a physical database, forming a further module 20, 28, 30, 50, 53 of the high power X-ray source apparatus 10 interconnected to the configuration control unit 60. The database can also be implemented as part of any one of the modules 20, 28, 30, 50, 53 of the high power X-ray source apparatus 10. The acceptable parameter set in the database can comprise any kind of information suitable for verifying the accuracy and/or origin of the identification parameters and/or operating parameters stored in the identification unit 25, 27, 31, 52, 54 of the module 20, 28, 30, 50, 53. As an example, the acceptable parameter set can comprise the name of the producer, the particular serial number, a particular deployment code or even the particular format or structure of data stored in the identification unit 25, 27, 31, 52, 54. In particular, the acceptable parameter set of the database can comprise single parameter values or whole ranges of acceptable parameter values (e.g. the minimum and the maximum operating voltage). The one or more modules 20, 28, 30, 50, 53 are authenticated at step F if the transmitted parameter or parameters of the one or various modules 20, 28, 30, 50, 53 match the acceptable parameter set of the database.

Finally, as already described above, the configuration control unit 60 can be implemented as a separate module 20, 28, 30, 50, 53 of the high power X-ray apparatus 10, but it can also be integrated in any one of the described modules 20, 28, 30, 50, 53. In particular, the configuration control unit 60 can be integrated into the controlling unit 40. Consequently, the configuration control unit 60 can also be implemented in a module exterior to the high power X-ray source 10, for example in a remote control device. Thus, the transmission of the identification parameters and/or operating parameters of one or various modules 20, 28, 30, 50, 53 from the respective identification unit 25, 27, 31, 52, 54 to the configuration control unit 60 can be implemented using any wireless transmission technology such as WLAN (IEEE 802.11), Bluetooth, ZigBee, infrared or any other wireless transmission technology. This transmission can be further secured using an encryption of data before transmitting them through the wireless (or even wired) link. For this purpose, any encryption method can be used.

It will be understood from the foregoing that the present invention presents a great advance in configuration of high power X-ray source apparatus (and any other X-ray source apparatus or X-ray source system) being set up having multiple modules by creating an automated method that provides for optimal and consistent configuration, thereby increasing significantly safety for the users, as well as convenience, while reducing at the same time risks related to possible material defects and thereby reducing potential costs connected with such defects and failures.

Other variations and modifications are possible without departing from the scope and spirit of the present invention as defined by the appended claims.

The invention claimed is:

1. A method for automated configuring of a high power X-ray source apparatus for activation to emit X-rays, the high power X-ray source apparatus being set up having a plurality of modules, each of said plurality of modules of the high power X-ray source apparatus comprises an identification unit, whereby identification and/or nominal parameters of the module are stored in the identification unit of a respective module, said method comprising:
- an acceptable set of different parameters for each of the plurality of modules is stored in a database of a configuration control unit;
- at least one identification and/or nominal parameter of each of the plurality of modules is transmitted from the identification unit of a respective module to the configuration control unit;
- the transmitted parameters of the plurality of modules are compared with the acceptable parameter set from the database of the configuration control unit and each module is authenticated if the transmitted parameters of the module match the acceptable parameter set of the database before activation of said high power X-ray source apparatus to emit X-rays;
- at least one operating parameter of at least one module is determined by the configuration control unit based on the transmitted parameters of the plurality of modules; and
- the high power X-ray source apparatus is automatically configured by setting to the at least one operating parameter that is determined by the configuration control unit of the module after each module is authenticated and then the high power X-ray source apparatus is activated to emit X-rays.

2. A method according to claim 1 further comprising:
at least one operating parameter of the at least one module is determined as the minimum of the transmitted parameters of the plurality of modules.

3. A method according to claim 1 further comprising:
the identification and/or nominal parameters of the module stored in the identification unit of the respective module comprise maximum operating voltage and/or maximum operating current and/or maximum operating power and/or maximum operating filament current and/or typical operating filament voltage.

4. A method according to claim 1 further comprising:
after configuring the high power X-ray source apparatus, at least one actual operating parameter of the module is stored in a continuous way in the identification unit of the respective module.

5. A method according to claim 1 further comprising:
the actual operating parameters of the module being stored in the identification unit of the respective module comprise the actual voltage and/or actual current and/or actual power and/or actual filament current.

6. A method according to claim 1 further comprising:
error log data are stored in the identification unit of the respective module.

7. A method according to claim 1 further comprising:
the acceptable parameter sets stored in the database of the configuration control unit comprise a value range.

8. A method according to claim 1 further comprising:
the transmitted parameters of the module are encrypted.

9. A method according to claim 1 further comprising:
the configuration control unit is external to the high power X-ray source apparatus.

10. A method according to claim 1 further comprising:
the configuration control unit is integrated in the module.

11. A method according to claim 1 further comprising:
at least one parameter of the module is transmitted to the configuration control unit wirelessly.

12. A method according to claim 1 further comprising:
the module is an X-ray tube.

13. A system for automated configuring of a high power X-ray source apparatus for activation to emit X-rays, the high power X-ray source apparatus being set up having plurality of modules each of said plurality of modules of the high power X-ray source apparatus comprises an identification unit, whereby identification and/or nominal parameters of the module are stored in the identification unit of the respective module, said system comprising:
- a configuration control unit with a database for storing an acceptable set of different parameters for each of the plurality of modules;
- each of the plurality of modules comprises a transmitter for transmitting at least one identification and/or nominal parameter of the respective module from the identification unit of the respective module to the configuration control unit;
- the configuration control unit comprises an authenticating system for comparing the transmitted parameters of the multiplicity of modules with the acceptable parameter set from the database, and for authenticating each module if the transmitted parameters of the module match the acceptable parameter set of the database before activation of said high power X-ray source apparatus to emit X-rays;
- the configuration control unit comprises an elaboration system for determining at least one operating parameter of at least one module based on the transmitted parameters of the plurality of modules; and
- the configuration control unit comprises a configuration system for automatically configuring the high power X-ray source apparatus by setting to the at least one operating parameter that is determined by the configuration control unit of the module after each module is authenticated and then activates the high power X-ray source apparatus to emit X-rays.

14. A system according to claim 13 further comprising:
the at least one operating parameter of the at least one module is determined as the minimum of the transmitted parameters of a plurality of modules.

15. A system according to claim 13 further comprising:
the identification and/or nominal parameters of the module stored in the identification unit of the respective module comprise maximum operating voltage and/or maximum operating current and/or maximum operating power and/or maximum operating filament current and/or typical operating filament voltage.

16. A system according to claim 13 further comprising:
the configuration control unit comprises a monitoring system for storing in a continuous way at least one actual operating parameter of the module in the identification unit of the respective module.

17. A system according to claim 16 further comprising:
the at least one actual operating parameter of the module being stored in the identification unit of the respective module comprise actual voltage and/or actual current and/or actual power and/or actual filament current.

18. A system according to claim 13 further comprising:
the configuration control unit comprises a monitoring system for storing in a continuous way error log data in the identification unit of the respective module.
19. A system according to claim 13 further comprising:
the acceptable parameter sets stored in the database of the configuration control unit comprise a value range.
20. A system according to claim 13 further comprising:
the transmitted parameters of the module are encrypted.
21. A system according to claim 13 further comprising:
the configuration control unit is external to the high power X-ray source apparatus.
22. A system according to claim 13 further comprising:
the configuration control unit is integrated in the module.
23. A system according to claim 13 further comprising:
the module comprises a transmitter for transmitting at least one parameter of the first module from the identification unit to a controlling module wirelessly.
24. A system according to claim 13 further comprising:
the module is an X-ray tube.
25. A device for automated configuring of a high power X-ray source apparatus for activation to emit X-rays, the high power X-ray source apparatus being set up having a plurality of modules, in which said plurality of modules of the high power X-ray source apparatus comprises an identification unit, whereby identification and/or nominal parameters of the module are stored in the identification unit of the respective module, said device comprising:
 a database for storing an acceptable set of parameters for the module;
 a receiver for receiving at least one identification and/or nominal parameter from the identification unit of each one of the plurality of modules;
 an authentication system for comparing the transmitted parameters of the plurality of modules with the acceptable parameter set from the database, and for authenticating each module if the transmitted parameters of the module match the acceptable parameter set of the database;
 an elaborating system for determining at least one operating parameter of at least one module based on the transmitted parameters of the plurality of modules; and
 a configuration system for automatically configuring the high power X-ray source apparatus by setting to the at least one operating parameter that is determined by the elaborating system of the module after each module is authenticated and then activates the high power X-ray source apparatus to emit X-rays.
26. A device according to claim 25 further comprising:
the at least one operating parameter of at least one module is determined by the elaboration system as the minimum of the transmitted parameters of the multiplicity of modules.
27. A device according to claim 25 further comprising:
the device is external to the high power X-ray source apparatus.
28. A device according to claim 25 further comprising:
the device is integrated in the module.

* * * * *